United States Patent [19]
Klein et al.

[11] Patent Number: 5,116,867
[45] Date of Patent: May 26, 1992

[54] D-PROPRANOLOL AS A SELECTIVE ADENOSINE ANTAGONIST

[75] Inventors: David C. Klein, Gaithersburg, Md.; Olga Nikodijevic, Suopje, Yugoslavia

[73] Assignee: The United States of America as represented by the Secretary of the Department of Health and Human Services, Washington, D.C.

[21] Appl. No.: 373,863

[22] Filed: Jun. 30, 1989

[51] Int. Cl.$^5$ .................... A61K 31/24; A61K 31/22; C07C 69/76; C07C 69/02
[52] U.S. Cl. .................... 514/534; 514/546; 560/106; 560/107; 560/129; 560/252; 560/231
[58] Field of Search ............... 560/106, 107, 129, 252, 560/231; 514/532, 546, 534

[56] References Cited

U.S. PATENT DOCUMENTS 3,534,085  10/1970  Narayanan et al. ............... 560/106

OTHER PUBLICATIONS

Grimes et al. Invest. Ophthalmol. 1972, 11(4) 231-5 Chemical Abstracts, vol. 77, 1972, Abstract 43303h.
Nilsson et al. Acta Endocrinol. 1980 94(1) 38-41 Chemical Abstracts vol. 93, 1980 Abs. 88913d.
Chasin et al., J. Biol. Chem. 246(9) pp. 3037-3041.
Farthing, et al. J. Antimicrobial Chemother. 1987 20(4) 519-22 Chemical Abstracts vol. 107, 1987, Abstract 232966a.

*Primary Examiner*—Cecilia Shen
*Attorney, Agent, or Firm*—Lowe, Price, LeBlanc & Becker

[57] ABSTRACT

Chemicals are disclosed which are useful for inhibiting the actions of adenosine in mammals, comprising: L-propranolol, or D-propranolol, or alprenolol and derivatives thereof for parenteral or topical administration are disclosed for purposes of achieving desired circulating concentrations in the range of 10 nanogram to 10 milligrams per kilogram.

D-Propranolol is of special interest because it is relatively inactive as a $\beta$-adrenergic blocking agent. Specific uses of D-propranolol include the treatment of asthma, chronic obstructive pulmonary disease, A-V node conduction disturbances; apnea of preterm infants, pulmonary hypertension, headaches, migraine, and in attention-deficit disorder. D-Propranolol might also be used as a substitute for xanthines in beverages to produce a feeling of well being, awakeness, awareness and increased performance.

16 Claims, 3 Drawing Sheets

D-PROPRANOLOL AS A SELECTIVE ADENOSINE ANTAGONIST

This invention provides a means of obtaining selective adenosine antagonist activity for use in treatment of illness.

BACKGROUND OF THE INVENTION

Figure 1:
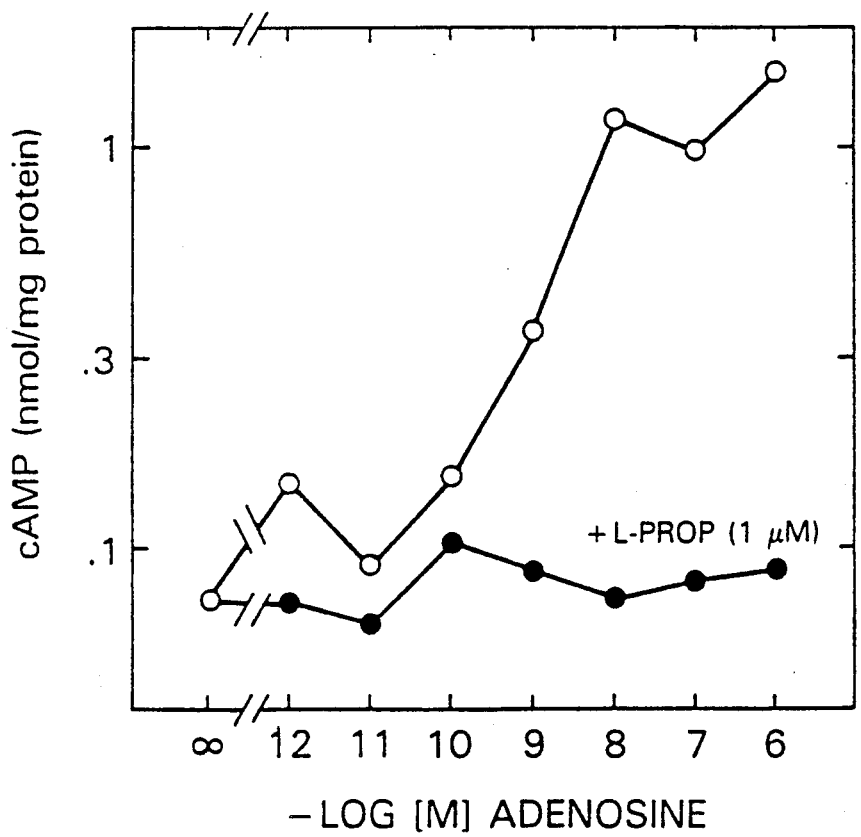

This invention relates to antagonists of adenosine (FIG. 1; review; Daly J, Bruns F, Snyder SH (1982)Life Sci 28 2083-2097), which is naturally occurring compound in life forms. Adenosine has been thought to regulate a broad range of biological processes as an extracellular regulating compound, functioning as a neurotransmitter or hormone (Bern RM, Rall TW, Rubio R(eds)(1983)Regulatory function of adenosine. Martinus Nijhoff, Boston, this a book available in the National Library of Medicine). For example, adenosine has been implicated in cardiovascular, fat cell metabolism and mental function. Adenosine is currently thought to act through interaction with the A2 adenosine receptor subtype, which mediates stimulation of cyclic AMP production by adenylyl cyclase, and/or through interaction with the A1 adenosine receptor subtype, which mediates inhibition of this enzyme (Londos C, Cooper DMF, Wolff J(1980) P.N.A.S. U.S.A. 27 2551-2554). The relative abundance of these receptors in any one tissue determines the effects of adenosine in that specific tissue.

Many of the currently available adenosine antagonists have been xanthines, including caffeine, 8-p-(sulfophenyl)theophylline and xanthine amine congener. These compounds have been recognized as being not as potent and as highly selective for either A1 or A2 receptors as would be needed for targeted activity. As a result, the effects of these compounds can reflect inhibition of both A1 and A2 effects. It is clearly preferred to have therapeutics which are able to selectively block either one or the other receptor. Very highly selective antagonists or agonists of A1 or A2 receptors have not been established.

Another limitation with some of these compounds is that they are not sufficiently potent. For example, at required concentrations they can act as inhibitors of phosphodiesterase.

SUMMARY OF THE INVENTION

The present invention identifies as adenosine antagonists both the D- and L-forms of propranolol which may be prepared by known methods (see Belg. pat 640,312 corresp to Crowther, Smith, U.S. Pat. No. 3,337,628 (1964, 1967 both to I.C.I.) and alprenolol (Neth. pat Appl. 6,605,692, 1966 to Aktiebolag Hassle; C.A. 66, 46214p, 1967; Neth. pat App 6,612,958, 1967 to ICI, C.A. 67,99851w, 1967. Alprenolol and L-propranolol have been known as beta blockers and are used to treat a broad range of diseases. These compounds share the same isopropylamino-2-propanolol side chain; propranolol has a naphthyl- ring structure and alprenolol has a phenyl-ring structure.

These compounds have been thought to act primarily by antagonizing receptor-mediated actions of catecholamines including norepinephrine and epinephrine. The mechanism of action has been thought to involve competition for sites on these membrane receptor molecules which mediate effects of these catecholamines. It is thought that occupancy of such sites by the compounds blocks the effects of catecholamines.

An important characteristic of the interaction of $\beta$-adrenergic antagonists and $\beta$-adrenergic receptors is that the interaction is specific for the L-form of the antagonist. Hence D-propranolol has been believed to be without effect at concentrations at which L-propranolol has therapeutic value; and further, in a wide variety of tests of adrenergic function and of characterization of beta-adrenergic receptors D-propranolol has been found to be 1/100 as potent as the L-form within the dynamic range of concentrations of the latter. A feature of the invention is that D-propranolol can be used to block effects of adenosine at concentrations which do not inhibit adrenergic systems. This provides the opportunity of using the D-form therapeutically to block effects of adenosine without blocking the effects of epinephrine or norepinephrine.

FIGURES

FIG. 1—Adenosine-cyclic AMP dose response curves in presence and absence of L-propranolo(L-PROP, 1 $\mu$M). Example 1. All drugs and chemicals were from commercial sources and were of the purest grade available. Pinealocytes were prepared from rat (Sprague-Dawley, 200 gm female) pineal glands by enzymatic and physical dispersion. Cells were maintained in Dulbecco's modified Eagle's Medium containing 10% fetal calf serum under an atmosphere of 95% oxygen and 5% $CO_2$ at 37° C. for 24 hours. Cells were then transferred to individual tubes ($10^5$ cells/0.5 ml) and treated with drugs of interest for 15 min. At the end of the treatment period, cells were collected by centrifugation (1000×g, 2 min) and placed on solid $CO_2$. Cyclic nucleotides were measured by radioimmunoassay in cell pellets (6,10). Protein in cell pellets was measured using a dye binding method with bovine serum albumin as a standard (11). Data are presented as the average of the means of duplicate determinations of cyclic AMP in each of three samples; mean values were within 20% of average.

Figure 2:
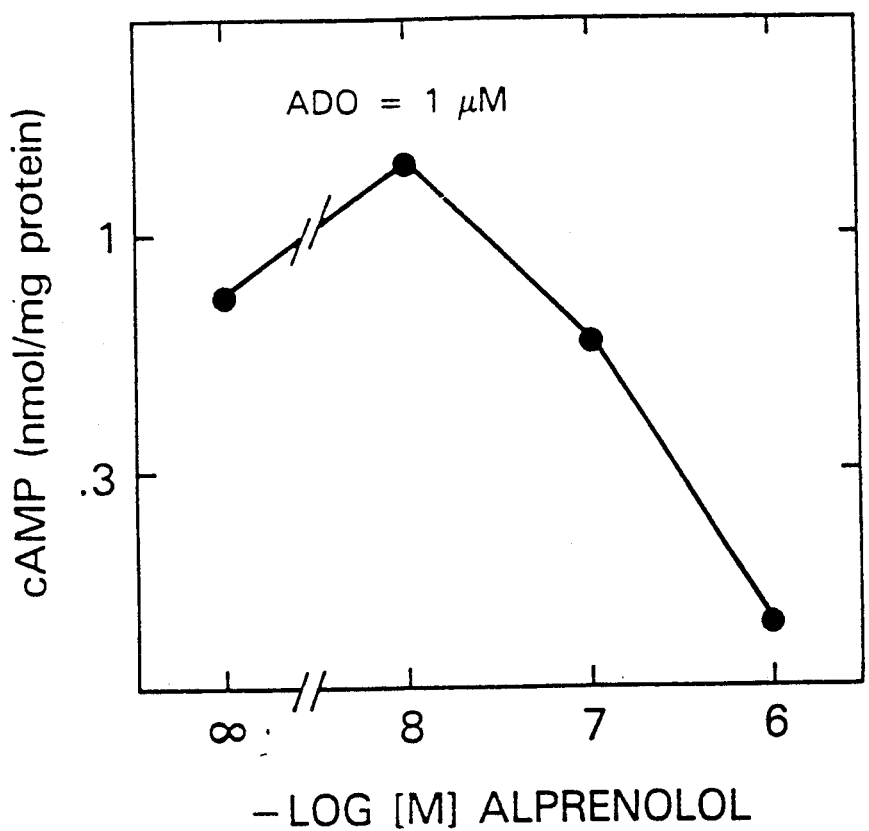

FIG. 2—Effects of alprenolol on adenosine (ADO, 1 $\mu$M) stimulation of cyclic AMP. For details see FIG. 1.

Figure 3:
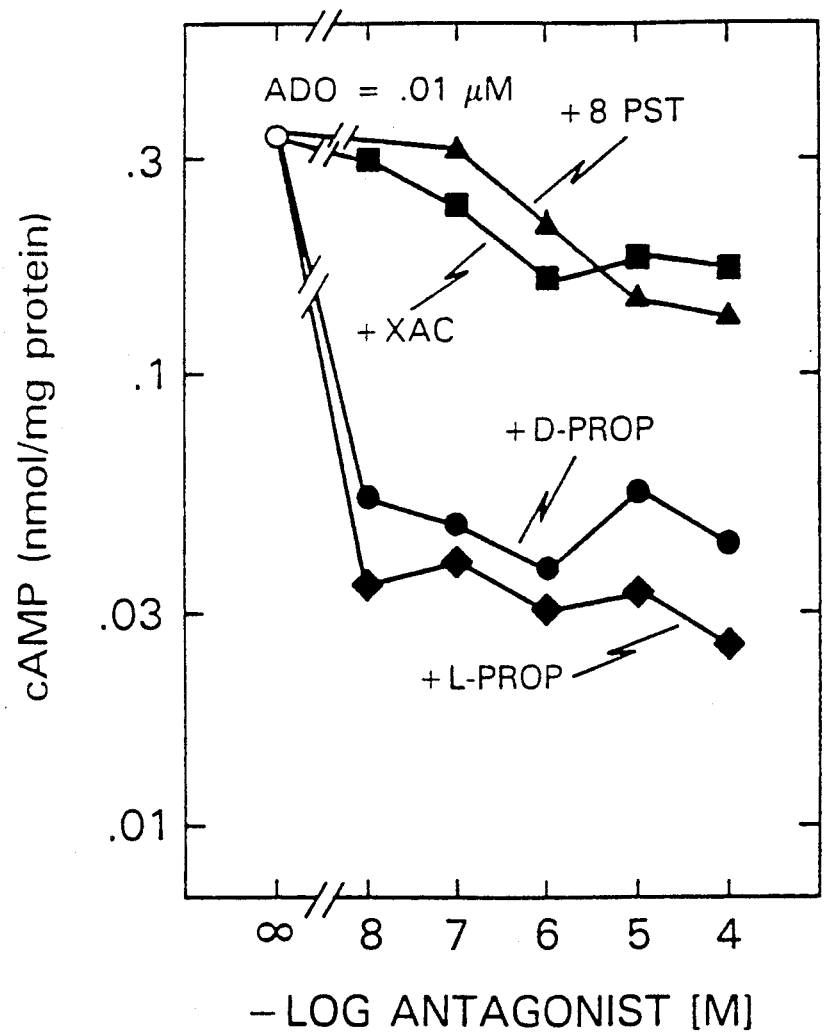

FIG. 3—Effects of D-propranolol, L-propranolol, xanthine amine congener(XAC) and p-(sulfophenyl)-theophylline, 8-PST) on adenosine (ADO, 10 nM) stimulation of cylcic AMP accumulation in pinealocytes. For details see FIG. 1.

DESCRIPTION OF INVENTION

As indicated herein, the potency of alprenolol, D-propranolol and L-propranolol as adenosine antagonists is high in comparison to other available adenosine antagonists. These chemicals act to inhibit effects of adenosine at low concentrations; and, can produce more complete inhibition of adenosine stimulation of cyclic AMP accumulation than can established adenosine antagonists.

This invention is of further special value because it identifies two compounds (propranolol and alprenolol) which do not belong to existing chemical families of adenosine antagonists. This invention thereby provides a chemical foundation for the development of a new family of adenosine antagonists containing the isopropylamino-2-propanol functional side chain, which is common to propranolol and alprenolol, and two subfamilies one of which derives from propranolol and the other from alprenolol. These new families may have therapeutic effects not provided by previously known antagonists.

The use of D-propranolol to inhibit the effects of adenosine without blocking of β-adrenergic receptors is of special importance, since the use of D-propranolol without blocking the effects of epinephrine or norepinephrine can provide an especially useful modality for treatment when the inhibition of adenosine-dependent processes is desirable and it is necessary to avoid effects associated with β-adrenergic blocking agents. One such side effect in certain individuals is drowsiness.

Specific uses of D-propranolol include the treatment of asthma, chronic obstructive pulmonary disease, A-V node conduction disturbances; apnea of preterm infants, pulmonary hypertension, headaches, migraine, and in attention-deficit disorder. D-Propranolol might also be used as a substitute for xanthines to produce a feeling of well being, awareness, awareness and increased performance in beverages to substitute for coffee, tea, colas and other drinks with xanthines.

Compositions of D-propranolol may be administered orally by usual means such as tablet, capsules, or solutions such as elixirs. Parenteral administration by usual means such as intravenous, intramuscular, or intradermal injection are also appropriate. Administration for absorption through local mucosa such as buccal, intranasal, or rectal administration are also appropriate and may be used to particular advantage to obtain rapid response in cases of apnea or asthmatic attack. Dosage range of 10 nanogram to 1 milligram per kilogram of weight is appropriate and will depend on the condition and age of the patient.

Compositions for selective adenosine antagonist activity should contain the propranolol wherein at least 85% is the D-propranolol isomer.

The parent propranolol molecule may be substituted for use in accord with the methods taught herein so long as the D isomer of the compound is used. Compounds of the class are those of the structure:

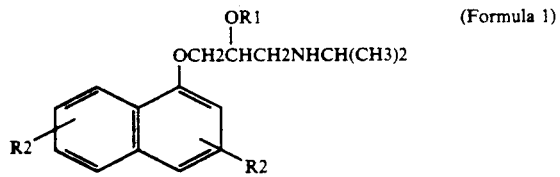

(Formula 1)

wherein $R_1$ is COH or COA, wherein A is alkyl or benzyl which may be substituted with halo, or hydroxy and wherein $R_2$ is alkyl, hydroxy, halo, or hydrogen atom, wherein at least 85% of the compounds is the D optical isomer or salts thereof in a pharmaceutical carrier.

EXAMPLES

The effect of these compounds is demonstrated in mammalian tissue such as the isolated rat pinealocyte by known methods (Klein DC, Weller J, Sugden AL, Sugden D, Vanecek J, Chik CL and Ho, AK (1988) in Fundamentals and Clinics in Pineal Research, Trentini, G.P., DeGaetani, C., and Pevet, P. (eds) Raven Press, New York pp 111-119) by treating cells with 10 nM adenosine and measuring the increase in cyclic AMP accumulation. In cells not treated with these new adenosine antagonists the increase in cyclic AMP is more than 50-fold. However, in cells which are treated with L-propranolol, D-propranolol, or alprenolol at a concentration of 1 μM for 15 minutes prior to and during adenosine treatment the increase in cyclic AMP is either not detectable or less than 2-fold (FIGS. 1-3). The relative effects of D-propranolol, L-propranolol, xanthine amine congener and 8-p-(sulfophenyl)theophylline are demonstrated in this system (FIG. 3).

We claim:

1. A method of inhibiting adenosine-dependent processes by administration to a mammal an adenosine-inhibiting effective amount of a composition of matter containing as an active ingredient a compound of the formula

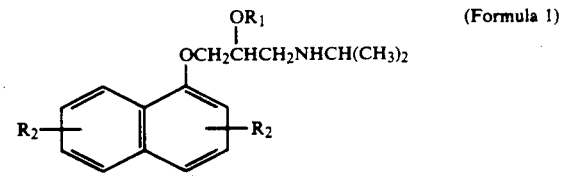

(Formula 1)

wherein $R_1$ is COH or COA, wherein A is alkyl or benzyl which may be substituted with halo or hydroxy and wherein $R_2$ is alkyl, hydroxy, halo, or hydrogen and wherein at least 85% of the compound is the D optical isomer or salts thereof.

2. A method of claim 1 wherein the active ingredient is D-Propranolol.

3. A method of claim 2 wherein the composition is in a form adapted for oral administration.

4. A method of claim 2 wherein the composition is in a form adapted for nasal administration.

5. A method of claim 2 wherein the composition is in a form adapted for buccal administration.

6. A method of claim 2 wherein the composition is in a form adapted for intravenous administration.

7. A method of claim 2 wherein the composition is in a form adapted for intradermal or intramuscular administration.

8. A composition of matter containing an effective adenosine-inhibiting amount of a compound of the formula:

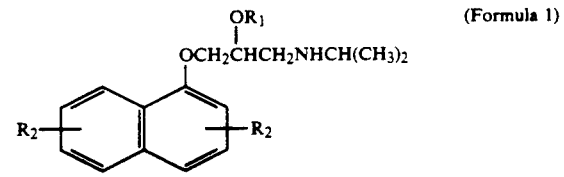

(Formula 1)

wherein $R_1$ is COH or COA, wherein A is alkyl or benzyl which may be substituted with halo or hydroxy and wherein $R_2$ is alkyl, hydroxy, halo, or hydrogen and wherein at least 85% of the compound is the D optical isomer or salts thereof.

9. A composition of matter containing as an active ingredient a compound of the formula:

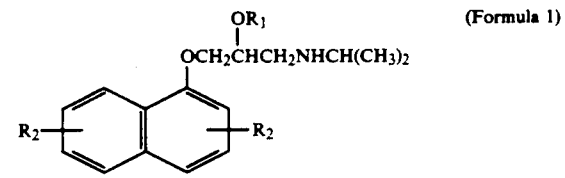

(Formula 1)

wherein $R_1$ is COH or COA, wherein A is alkyl or benzyl which may be substituted with halo or hydroxy and wherein $R_2$ is alkyl, hydroxy, halo, or hydrogen;

and wherein at least 85% of the compound is the D optical isomer or salts thereof in a carrier adapted for intranasal administration.

10. A composition of matter containing as an active ingredient a compound of the formula:

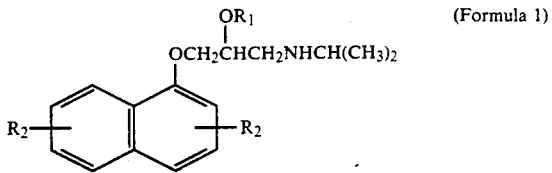
(Formula 1)

wherein $R_1$ is COH or COA, wherein A is alkyl or benzyl which may be substituted with halo or hydroxy and wherein $R_2$ is alkyl, hydroxy, halo, or hydrogen;

and wherein at least 85% of the compound is the D optical isomer or salts thereof in a carrier adapted for administration by mouth.

11. A composition of claim 10 which is a tablet.

12. A composition of claim 10 which is a capsule.

13. A composition of matter containing as an active ingredient a compound of the formula:

(Formula 1)

wherein $R_1$ is COH or COA, wherein A is alkyl or benzyl which may be substituted with halo or hydroxy and wherein $R_2$ is alkyl, hydroxy, halo, or hydrogen;

and wherein at least 85% of the compound is the D optical isomer or salts thereof in a carrier adapted for parenteral administration.

14. A composition of claim 10 which is a composition in the form of an elixir that is adapted for administration by mouth.

15. A method of claim 1 wherein said compound is used in concentrations which substantially do not inhibit adrenergic systems.

16. A composition of claims 8, 9, 10 or 13 wherein the composition is in an amount sufficient to provide a concentration of $10^{-8}$ Molar to $10^{-6}$ Molar in said patient.

* * * * *